(12) United States Patent
Zhang et al.

(10) Patent No.: US 10,799,612 B2
(45) Date of Patent: Oct. 13, 2020

(54) IMPLANTED DEVICE

(71) Applicant: Lifetech Scientific (Shenzhen) Co., Ltd., Shenzhen (CN)

(72) Inventors: Deyuan Zhang, Shenzhen (CN); Liping Chen, Shenzhen (CN); Haiping Qi, Shenzhen (CN); Hongtao Sun, Shenzhen (CN); Jun Hu, Shenzhen (CN); Wenjiao Lin, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 0 days.

(21) Appl. No.: 16/068,122

(22) PCT Filed: Jun. 27, 2016

(86) PCT No.: PCT/CN2016/087291
§ 371 (c)(1),
(2) Date: Jul. 4, 2018

(87) PCT Pub. No.: WO2017/117922
PCT Pub. Date: Jul. 13, 2017

(65) Prior Publication Data
US 2019/0008996 A1  Jan. 10, 2019

(30) Foreign Application Priority Data
Jan. 8, 2016 (CN) .......................... 2016 1 0016894

(51) Int. Cl.
| | |
|---|---|
| *A61L 27/04* | (2006.01) |
| *A61L 31/14* | (2006.01) |
| *A61F 2/82* | (2013.01) |
| *C22C 18/00* | (2006.01) |
| *A61F 2/02* | (2006.01) |
| *C22C 1/02* | (2006.01) |
| *A61L 27/00* | (2006.01) |
| *C22F 1/16* | (2006.01) |
| *A61B 17/68* | (2006.01) |
| *A61K 6/84* | (2020.01) |
| *A61P 37/08* | (2006.01) |
| *A61P 29/00* | (2006.01) |
| *A61K 45/06* | (2006.01) |
| *A61L 27/42* | (2006.01) |
| *A61L 27/58* | (2006.01) |
| *A61L 31/02* | (2006.01) |
| *C07F 3/06* | (2006.01) |
| *A61L 31/00* | (2006.01) |

(52) U.S. Cl.
CPC ............ *A61L 27/047* (2013.01); *A61B 17/68* (2013.01); *A61F 2/02* (2013.01); *A61F 2/82* (2013.01); *A61K 6/84* (2020.01); *A61K 45/06* (2013.01); *A61L 27/00* (2013.01); *A61L 27/427* (2013.01); *A61L 27/58* (2013.01); *A61L 31/022* (2013.01); *A61L 31/148* (2013.01); *A61P 29/00* (2018.01); *A61P 37/08* (2018.01); *C07F 3/06* (2013.01); *C22C 1/02* (2013.01); *C22C 18/00* (2013.01); *C22F 1/16* (2013.01); *A61F 2002/823* (2013.01); *A61F 2220/0016* (2013.01); *A61F 2240/001* (2013.01); *A61L 27/045* (2013.01); *A61L 31/005* (2013.01)

(58) Field of Classification Search
CPC ........ A61L 31/48; A61L 27/58; A61L 31/022; A61L 31/16; A61L 27/045; A61F 2002/823; A61K 6/84; C22C 18/00
See application file for complete search history.

(56) References Cited

U.S. PATENT DOCUMENTS

| | | | | |
|---|---|---|---|---|
| 2005/0234538 A1* | 10/2005 | Litvack | ................... | A61F 2/958 623/1.11 |
| 2007/0244548 A1* | 10/2007 | Myers | ..................... | A61L 27/28 623/1.42 |
| 2008/0262589 A1 | 10/2008 | Nagura | | |
| 2009/0093875 A1* | 4/2009 | Stalker | .................. | A61L 31/022 623/1.42 |
| 2009/0187258 A1 | 7/2009 | Ip | | |
| 2010/0076544 A1* | 3/2010 | Hoffmann | ............. | A61L 31/022 623/1.15 |

(Continued)

FOREIGN PATENT DOCUMENTS

| | | |
|---|---|---|
| CN | 101283992 A | 10/2008 |
| CN | 101077862 B | 4/2011 |
| CN | 102596277 A | 7/2012 |

(Continued)

OTHER PUBLICATIONS

International Search Report dated Oct. 10, 2016 for corresponding PCT Application No. PCT/CN2016/087291.

(Continued)

*Primary Examiner* — Tracy Liu
(74) *Attorney, Agent, or Firm* — Raymond Sun

(57) ABSTRACT

Disclosed is an implanted device, comprising a device base body and an active drug, wherein the device base body is pure zinc and/or a zinc alloy, the zinc content in the device base body is 0.1-100%, and the active drug comprises anti-allergic drugs. After the implantation of the implanted device into the human body, the surrounding tissues of the implant would not have a clear hypersensitive reaction due to the presence of the anti-allergic drugs, and the implanted device can be used to be implanted into the body for supporting organ chambers, to fill the hollow chambers of the organs and tissues or as orthopaedic implants etc.

3 Claims, 4 Drawing Sheets

(56) References Cited

U.S. PATENT DOCUMENTS

2012/0071967 A1* 3/2012 Tarcha .................... A61L 31/10
623/1.46

FOREIGN PATENT DOCUMENTS

| CN | 103948458 A | * | 7/2014 |
| CN | 104212998 A | | 12/2014 |
| CN | 104587534 A | | 5/2015 |
| CN | 105648272 A | | 6/2016 |
| WO | WO2008122596 A2 | | 10/2008 |

OTHER PUBLICATIONS

Wen, Liping et al. "Hypersensitivity to Implanted Devices: a Double-bladed Sword of High-tech?—From the Allergy Point of View", Journal of Allergy and Clinical Immunology, vol. 3, No. 1, Mar. 31, 2009, pp. 9-15, IV, p. 11, left-hand col., paras. 1 and 4.
Office Action for corresponding China Application No. 201610016894.2.

* cited by examiner

IMPLANTED DEVICE

TECHNICAL FIELD

The present application relates to the field of medical devices, and more particularly relates to an implanted device.

BACKGROUND ART

At present, an implanted medical device is generally made of a metal and an alloy thereof, ceramic, a polymer and a relevant composite material, wherein a metal material-based implanted medical device is particularly preferred for its excellent mechanical properties such as high intensity and toughness.

At present, in the field of cardiovascular implantation, a vascular stent is generally made of a non-degradable metal, but this stent suffers from the defect that the metal does not degraded and the stent cannot be taken out, so mat the metal retained in a blood vessel easily causes many future adverse events, such as a late thrombus. Therefore, an implanted medical device made of a corrodible and degradable metal material, such as zinc and iron, have good application potential. An absorbable stent with zinc as a substrate material has good flexibility and biocompatibility, and zinc ions also have anti-oxidation and endothelium stabilizing effects; and meanwhile, zinc ions are transported very rapidly in a human tissue, so that no zinc enrichment and no cytotoxicity or necrocytosis will result near to a zinc-based implanted device.

Zinc also may be applied to the field of orthopedic implanted devices. As the zinc ions may activate aminoacyl tRNA synthetase in osteoblast, and may effectively inhibit differentiation and growth of osteoclast, the presence of the zinc ions promotes increase in the content of bone calcium salt, and is also favorable for increasing the content of the bone collagen, which indicates that the zinc ions have a function of directly promoting the growth of bone tissues. In addition, the zinc ions also may promote combination between cartilage oligomeric matrix protein and collagen, and are catalytic elements for cartilage growth and regeneration. A zinc-based degradable bone nail may release about 0.2 to 0.3 mg of zinc per day, and an adult may have a toxic reaction after taking about 300 mg of zinc per day, so that the zinc ions released by degradation of the zinc-based degradable orthopedic implanted device will likely not cause general toxicity.

It is necessary for an implanted device to have good biocompatibility and low toxicity or no toxicity, and to meet clinical safety requirements. For zinc-containing implanted devices, it is desired to reduce the early safety risk of zinc after implantation, but this problem has not been successfully solved.

SUMMARY OF THE INVENTION

After a zinc-containing implanted device is implanted, a sensitization reaction might possibly be caused in local tissues in the early stage, for example, a zinc-containing vascular stent may possibly cause a sensitization reaction in surrounding vascular tissues after being implanted into a blood vessel, and then cause stent blocking and even more serious mortality risks, thereby posing a serious potential safety hazard. We think that this early sensitization reaction is caused by free zinc ions generated by the corrosion of pure zinc or a zinc alloy itself in the body. The objective of the present application is to reduce the above-mentioned safety risk of the zinc-containing implanted device. The implanted device of the present application may be implanted into the body to support lumens (such as a vascular stent), or to fill hollow organ tissues (such as an occluder), or to be used as an orthopedic implant and the like.

The technical solution of the present application is as follows:

The present application provides an implanted device, including a device substrate and an active drug. The device substrate is pure zinc and/or a zinc alloy; the device substrate contains 0.1 to 100 percent of zinc, and the active drug includes an anti-allergic drug. The zinc alloy is a medical zinc-based alloy, and is composed of zinc and a nutrient element or low-toxicity element in the human body. The nutrient element or low-toxicity element in the human body is selected from the group consisting of iron, magnesium, calcium, sodium, copper, manganese, chromium, selenium, molybdenum, cobalt, nickel, vanadium, tin, silicon, strontium, boron, cerium, lithium and potassium.

In one embodiment, the implanted device further includes a zinc complexing agent. The zinc complexing agent and the pure zinc or zinc alloy in the device substrate form a complex in body fluid. The complexing agent is also known as a ligand, and structurally contains a coordination group capable of providing lone pair electrons or π electrons. The zinc complexing agent may generate complex reaction with divalent zinc ions serving as corrosion products in a pure zinc and/or zinc alloy corrosion process to reduce the number of the free zinc ions, so that no obvious sensitization reaction is caused in tissues around the implant.

In one embodiment, the zinc complexing agent contains at least one coordination group; the coordination group is selected from the group consisting of hydroxyl on polycyclic aromatic hydrocarbon, sulfydryl, amino, an aromatic heterocyclic group, nitroso, carbonyl, sulpho, a phosphate group and an organic phosphorus group. The hydroxyl on the polycyclic aromatic hydrocarbon is a phenolic hydroxyl group. The aromatic heterocyclic group is selected from the group consisting of furyl, pyrryl, imidazolyl, triazolyl, thienyl, thiazolyl, pyridyl, a pyridone group, pyranyl, a pyrone group, pyrimidyl, pyridazinyl, pyrazinyl, quinolyl, isoquinolyl, phthalazinyl, pteridyl, indolyl, purinyl and a phenanthroline group.

In one embodiment, the zinc complexing agent is selected from the group consisting of: a hydroxyl-on-polycyclic aromatic hydrocarbon-containing polydentate ligand including 8-hydroxyquinoline, 8-hydroxyquinaldine, 4,5-dioxybenzene-1,3-sodium disulfonate, 4-[3,5-bis-hydroxyphenyl-1H-1,2,4-triazole]-benzoic acid and 1-(2-pyridine azo)-2-naphthol; a sulfydryl-containing complexing agent including 8-mercaptoquinoline, mercaptoacetic acid, propyl disulfide and 5-methyl-2-mercapto mercaptobenzoate; an amido-containing complexing agent including ethidene diamine, triethylene tetramine, ethylenediamine tetraacetic acid, ethylene diamine tetraacetic acid tetrasodium, triethylene tetramine and N-(2-ethoxyl)ethidene diamine-N,N', N'-triacetic acid or N'-[5-[[4-[[5-(acetyl hydroxylamine) amyl]ammonia]-1,4-dioxo butyl]hydroxylamine]amyl]-N-(5-amido amyl)-N-hydroxyl succinimide; an aromatic heterocyclic group-containing complexing agent including phenanthroline, dipyridyl, porphyrin, porphin, chlorophyll, hemoglobin or 1,2-dimethyl-3-hydroxyl-4-pyridone; a nitroso-containing polydentate ligand including 1-nitroso-2-naphthol or 1-nitroso-2-naphthol-6-sodium sulfonate; a sulpho-containing polydentate ligand including sulfosalicylic acid or 8-Hydroxyquinoline-5-sulphonic acid, a phosphate group-containing polydentate ligand including pyrophosphoric acid, tripolyphosphoric acid, hexametaphosphoric acid, polyphosphoric acid, sodium pyrophosphate, sodium hexametaphosphate or ammonium polyphosphate; an organic phosphorus-containing complexing agent including potassium diethylenetriamine pentamethylene phosphonate or sodium ethylenediamine tetramethylene phosphonate; a carbonyl-containing ligand including carboxylic acid and salt thereof, anhydride, ester, amide, polycarboxylic acid or polyanhydride, and further the carbonyl-containing ligand including gluconic acid, oxalic acid, tartaric acid, malic acid, oxaloacetic acid, fumaric acid, maleic acid, citric acid, nitrilotriacetic acid, diethylene triamine pentacarboxylic acid, alginic acid, glutamic acid, aspartic acid, ornithine, lysine, 1,2-diaminocyctohexane-N,N,N',N'-tetraacetic acid, potassium citrate, calcium citrate, monoglyceride citrate, acetylsalicylic acid, sulpho salicylamide, polyaspartic acid, polyglutamic acid, poly-ornithine, polylysine or polymaleic anhydride.

In one embodiment, the anti-allergic drug is selected from the group consisting of an antihistamine type anti-allergic drug, an ontileukotriens drug, a mast cell membrane stabilizer, a glucocorticoids anti-allergic drug or an immunoregulation anti-allergic drug.

In one embodiment, the anti-allergic drug is selected from the group consisting of chlortrimeton, diphenhydramine, promethazine hydrochloride, cetirizine, clarityne, mizolastine, ebastine, astemizole, terfenadine, desloratadine, fexofenadine, cyproheptadine, ketotifen, levocetirizine, meclizine, efletirizine, carebastine, azelastine, decloxizine, chlorcyclizine, amlexanox, acrivastine, azatadine, mequitazine, levocabastine, setastine, sequifenadine, deptropine, pizotifen, pyrilamine, ranitidine, emedastine, epinastine, promethazine, montelukast, zafirlukast, tomelukast, zileuton, amlexanox, ibudilast, pemirolast, doxepin, verlukast, docebenone, sodium cromoglycate, sodium hydroxypropylcromate, nedocromil sodium, tranilast, tiaramide, repirinast, bufrolin, zaprinast, tazanolast, ozagrel, repirinast, dexamethasone, methylprednisolone, hydrocortisone, triamcinolone acetonide, corticosteroids, vitamin C, calcium, coenzyme Q10 or trypsin chymotrypsin.

In one embodiment, the content of the anti-allergic drug on the surface of the device substrate ranges from 10 to 500 ug/cm$^2$, and in particular 100 to 300 ug/cm$^2$.

In one embodiment, the active drug further includes at least one of an anti-restenosis drug, an anti-hyperplasia drug, an antiplatelet drug or an anti-inflammatory reaction drug.

In one embodiment, the active drug is in contact with the device substrate in at least one of the following manners: the active drug at least partially covers the surface of the device substrate; or the device substrate has micro pores, and the active drug is arranged in the micro pores of the device substrate; or the device substrate is provided with a gap, a hole or a groove, and the active drug is arranged in the gap, the hole or the groove of the device substrate; or the device substrate has an inner cavity, and the inner cavity of the device substrate is filled with the active drug.

In one embodiment, the active drug exists in the form of a coating. The coating has a thickness in the range of 2 to 50 μm thickness, and in particular 5 to 25 μm.

In one embodiment, the coating further includes a polymer carrier. The polymer carrier is a degradable polymer, and the degradable polymer is formed by physically blending one or several of polylactic acid, polyglycolic acid, poly(ethylene succinate), poly(beta-hydroxybutyrate), polycaprolactone, polyethylene glycol adipate, a polylactic acid-glycollic acid copolymer or polypentanoate, or is formed by copolymerizing one or several of the polylactic acid, the polyglycolic acid, the poly(ethylene succinate), the poly(beta-hydroxybutyrate), the polycaprolactone, the polyethylene glycol adipate, the polylactic acid-glycollic acid copolymer or the polypentanoate. Or the polymer carrier is a nondegradable polymer, and the nondegradable polymer is formed by physically blending one or several of polyurethane, polycarbonate, poly(methyl methacrylate), polystyrene, polybutylene or poly(butyl methacrylate), or is formed by copolymerizing one or several of the polyurethane, the polycarbonate, the poly(methyl methacrylate), the polystyrene, the polybutylene or the poly(butyl methacrylate). Or the polymer carrier is formed by physically blending one or several of monomers of the degradable polymers and monomers of the nondegradable polymers, or is formed by copolymerizing one or several of the monomers of the degradable polymers and the monomers of the nondegradable polymers.

In one embodiment, a mass ratio of the polymer carrier to the active drug ranges from 50:1-1:20, and in particular 10:1-1:10.

In one embodiment, the implanted device is a stent, an occluder, an orthopedic implant, a dental implant, a suture line or a bolt.

In one embodiment, the stent is a vascular stent, a tracheal stent, an esophageal stent, a urethral stent, an intestinal stent or a biliary stent.

In one embodiment, the orthopedic implant is a fixing screw, a fixing rivet or a bone plate.

When the implanted device provided by the present application includes the zinc complexing agent, but does not include the active drug, the implanted device may still show low sensitization risk to the surrounding tissues, which indicates that the zinc complexing agent also reduces the sensitization effect of the zinc on the tissues.

Compared with the prior art, the present application has the following advantages and beneficial effects:

By use of the implanted device of the present application, it is a first discovery in the industry that the pure zinc or zinc alloy might cause sensitization by its corrosion, and the anti-allergic drug is first used to inhibit the sensitization effect caused by the corrosion of the pure zinc or zinc alloy after the pure zinc or zinc alloy-containing implanted device is implanted into the human body, thereby reducing the potential safety hazard of the implant, and solving the technical problem of the tissue sensitization risk of the zinc-containing implanted device, which addresses a long-felt need in the field, but which has not been successfully solved.

DETAILED DESCRIPTION OF THE INVENTION

For the purpose of making objectives, technical solutions and advantages of the present application clearer, a further detailed description will be made below to the present application in conjunction with accompanying drawings and embodiments. It should be understood that the specific embodiments described herein are merely explanatory of the present application, but not intended to limit the present application.

Unless otherwise specified, all technical and scientific terms used in this text are the same as meanings of general understandings of technical persons skilled in the art of the present application. The terms used in the description are merely descriptive of the objectives of the specific embodiments, but not intended to limit the present application.

Contrast 1

A vascular stent which takes pure zinc as a substrate is implanted into a porcine coronary blood vessel, and the device substrate of the vascular stent contains 100 percent of zinc. After 6 months, the stent and vascular tissue where the stent is implanted are taken out, and the vascular tissue is subjected to pathology observation.

Figure 1:
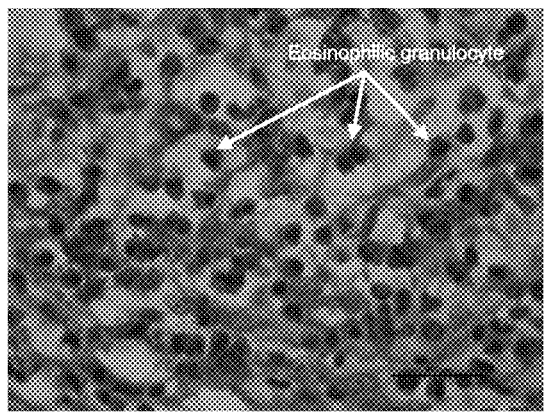
FIG. 1 is a sensitization pathological section of a tissue around a vascular stent of Contrast 1 after the stent has been implanted into a porcine coronary blood vessel for 6 months.

With reference to FIG. 1, a pathological section shows that the vascular tissue around the vascular stent of Contrast 1 generates a large number of eosinophilic granulocytes, that is to say, the pure zinc-based vascular stent of this contrast has an obvious sensitization effect on the implantation tissue.

Contrast 2

A vascular stent which takes an iron-zinc alloy as a substrate is implanted into a porcine coronary blood vessel, and the device substrate of the vascular stent contains 70 percent of zinc, 25 percent of iron, 3.5 percent of magnesium, 0.5 percent of calcium, 0.2 percent of copper and the balance of inclusion elements. After 6 months, the stent and vascular tissue where the stent is implanted are taken out, and the vascular tissue is subjected to pathology observation.

Figure 2:
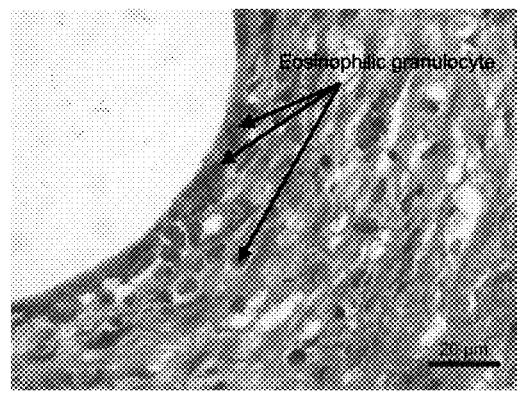
FIG. 2 is a sensitization pathological section of a tissue around a vascular stent of Contrast 2 after the stent has been implanted into a porcine coronary blood vessel for 6 months.

With reference to FIG. 2, a pathological section shows that the vascular tissue around the vascular stent of Contrast 2 generates a large number of eosinophilic granulocytes, that is to say, the iron-zinc alloy vascular stent of this contrast has an obvious sensitization effect on the implantation tissue.

Embodiment 1

A vascular stent has an iron-zinc alloy as a substrate, and the device substrate of the vascular stent contains 95 percent of zinc, 4.5 percent of iron and total 0.5 percent of inclusion elements except for the zinc and the iron. The surface of the stent is coated with a mixture of polylactic acid, dexamethasone and gluconic acid by dripping; after the surface is dried, the vascular stent of Embodiment 1 is obtained; a coating on the surface of the stent is 2 μm in thickness, and the mass ratio of the polylactic acid to the dexamethasone in the coating is 2:1; and the content of the dexamethasone drug on the surface of the device substrate is 100 ug/cm$^2$. The vascular stent of this embodiment is implanted into a porcine coronary blood vessel. After 6 months, the stent and vascular tissue where the stent is implanted are taken out, and the vascular tissue is subjected to pathology observation.

Figure 3:
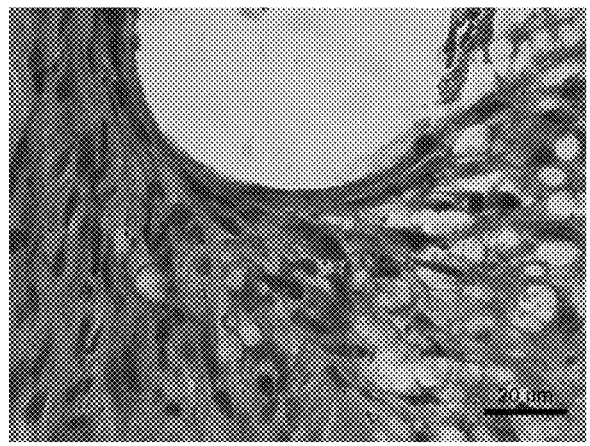
FIG. 3 is a pathological section of a tissue around a vascular stent of Embodiment 1 after the stent has been implanted into a porcine coronary blood vessel for 6 months.

With reference to FIG. 3, a pathological section shows that the vascular tissue around the vascular stent of this embodiment does not generate eosinophilic granulocytes, that is to say, the vascular stent of this embodiment has no sensitization effect on the implantation tissue.

The vascular stent of this embodiment contains the dexamethasone which serves as an anti-allergic drug and the gluconic acid which is capable of generating a complex together with the zinc; after the vascular stent is implanted into the vascular tissue, the dexamethasone inhibits the sensitization effect of the zinc alloy in the device substrate of the vascular stent on the vascular tissue through its pharmaceutical effect. In addition, the gluconic acid is in complexation with zinc ions which are corrosion products of the iron-zinc alloy, thereby reducing the number of free zinc ions and further reducing the sensitization risk of the implant.

Embodiment 2

A stent has pure zinc as a substrate, and the device substrate of the stent contains 99.95 percent of zinc and the balance of inclusion elements. The surface is subjected to dip-coating in a mixture of polyglycolic acid, methylprednisolone, ethylene diamine tetraacetic acid tetrasodium and sirolimus; the mass ratio of three components in the mixture is 50:1:1 and a coating with the thickness of 25 μm is obtained; after the coating is dried, the vascular stent of Embodiment 2 is obtained; and the content of the methylprednisolone drug on the surface of the device substrate is 200 ug/cm$^2$. The vascular stent of this embodiment is implanted into a porcine coronary blood vessel. After 6 months, the stent and vascular tissue where the stent is implanted are taken out, and the vascular tissue is subjected to pathology observation.

Figure 4:
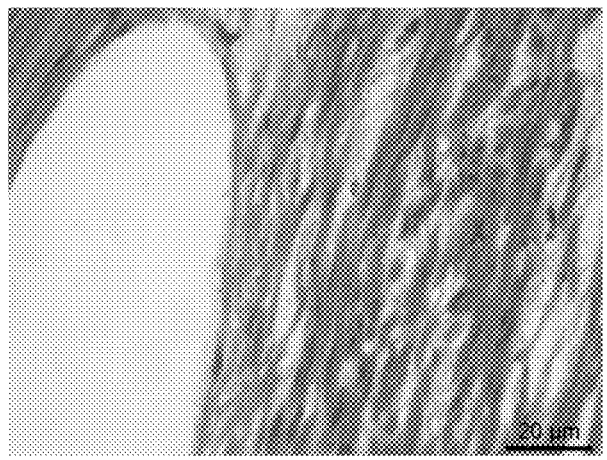
FIG. 4 is a pathological section of a tissue around a vascular stent of Embodiment 2 after the stent has been implanted into a porcine coronary blood vessel for 6 months.

With reference to FIG. 4, a pathological section shows that the vascular tissue around the vascular stent of this embodiment does not generate eosinophilic granulocytes, that is to say, the vascular stent of this embodiment has no sensitization effect on the implantation tissue.

The vascular stent of this embodiment contains the methylprednisolone which serves as an anti-allergic drug and ethylene diamine tetraacetic acid which is capable of generating a complex together with the zinc; after the vascular stent is implanted into the vascular tissue, the methylprednisolone inhibits the sensitization effect of the pure zinc in the device substrate of the vascular stent on the vascular tissue through its pharmaceutical effect. In addition, the ethylene diamine tetraacetic acid tetrasodium salt is in complexation with zinc ions which are corrosion products of the device substrate, thereby reducing the number of free zinc ions and further reducing the sensitization risk of the implant.

Embodiment 3

A galvanized iron-based stent is provided and the device substrate of the stent contains 1 percent of zinc, 98 percent of iron and the balance of inclusion elements. The surface of the device substrate is first coated with a solution containing polylactic acid-glycollic acid, hydrocortisone and acetylsalicylic acid via spraying, thus obtaining a coating with the thickness of 50 μm: the mass ratio of the polylactic acid-glycollic acid to the hydrocortisone in the coating is 1:5; then the surface of the drug coating is coated with a polylactic acid coating layer with a thickness of 5 μm, thus obtaining a vascular stent of Embodiment 3; and the content of the hydrocortisone drug on the surface of the device substrate is 300 ug/cm$^2$. The vascular stent of this embodiment is implanted into a porcine coronary blood vessel. After 1 month, the stent and vascular tissue where the stent is implanted are taken out, and the vascular tissue is subjected to pathology observation.

Figure 5:
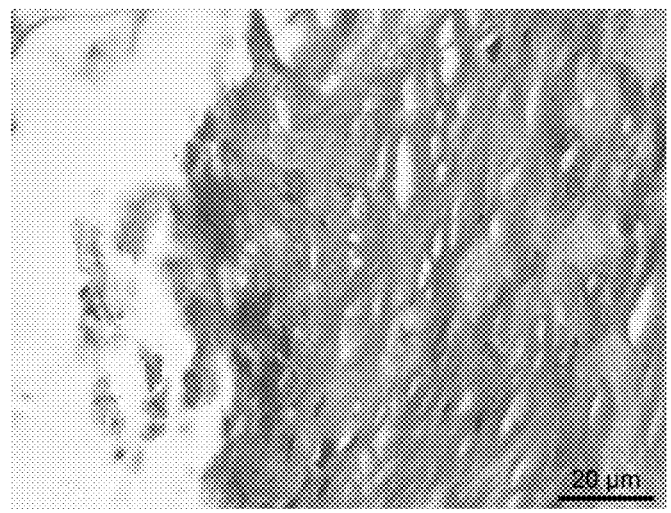
FIG. 5 is a pathological section of a tissue around a vascular stent of Embodiment 3 after the stent has been implanted into a porcine coronary blood vessel for 1 month.

With reference to FIG. 5, a pathological section shows that the vascular tissue around the vascular stent of this embodiment does not generate eosinophilic granulocytes, that is to say, the vascular stent of this embodiment has no sensitization effect on the implantation tissue.

The vascular stent of this embodiment contains the hydrocortisone which serves as an anti-allergic drug and the acetylsalicylic acid which is capable of generating a complex together with the zinc; after the vascular stent is implanted into the vascular tissue, the hydrocortisone inhibits the sensitization effect of the pure zinc in the device substrate of the vascular stent on the vascular tissue through its pharmaceutical effect. In addition, the acetylsalicylic acid is in complexation with zinc ions, thereby reducing the number of free zinc ions and further reducing the sensitization risk of the implant.

Embodiment 4

A vascular stent with a groove in the surface is provided, the device substrate of the stent is an alloy containing zinc, magnesium and iron, and contains 40 percent of zinc, 50 percent of iron, 9.5 percent of magnesium and the balance of inclusion elements. The outer surface of the stent and the inside of the groove are coated with a mixture of polystyrene, 8-hydroxyquinoline and levocetirizine by dripping, thus obtaining a coating with the thickness of 25 μm; the mass ratio of the polystyrene to the levocetirizine in the coating is 1:1, and a vascular stent of Embodiment 4 is obtained; and the average content of the levocetirizine drug on the surface of the device substrate is 50 ug/cm$^2$. The vascular stent of this embodiment is implanted into a porcine coronary blood vessel. After 3 months, the stent and vascular tissue where the stent is implanted are taken out, and the vascular tissue is subjected to pathology observation.

Figure 6:
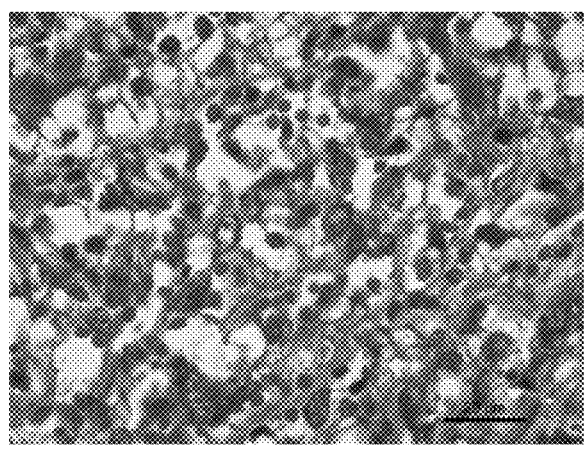
FIG. 6 is a pathological section of a tissue around a vascular stent of Embodiment 4 after the stent has been implanted into a porcine coronary blood vessel for 3 months.

With reference to FIG. 6, a pathological section shows that the vascular tissue around the vascular stent of this embodiment does not generate eosinophilic granulocytes, that is to say, the vascular stent of this embodiment has no sensitization effect on the implantation tissue.

The vascular stent of this embodiment contains the levocetirizine which serves as an anti-allergic drug and the 8-hydroxyquinoline which is capable of generating a complex together with the zinc; after the vascular stent is implanted into the vascular tissue, the levocetirizine inhibits the sensitization effect of the zinc alloy in the device substrate of the vascular stent on the vascular tissue by its pharmaceutical effect. In addition, the 8-hydroxyquinoline is in complexation with zinc ions, thereby reducing the number of free zinc ions and further reducing the sensitization risk of the implant.

Embodiment 5

A zinc-manganese-magnesium alloy vascular stent is provided, its device substrate contains 20 percent of zinc, 5 percent of manganese and 75 percent of magnesium. Multiple gaps are distributed on the surface of the stent, and are filled with dexamethasone, thus obtaining the vascular stent of Embodiment 5; and the content of the dexamethasone drug on the surface of the device substrate is 500 ug/cm$^2$. The vascular stent of this embodiment is implanted into a porcine coronary blood vessel. After 6 months, the stent and vascular tissue where the stent is implanted are taken out, and the vascular tissue is subjected to pathology observation.

Figure 7:
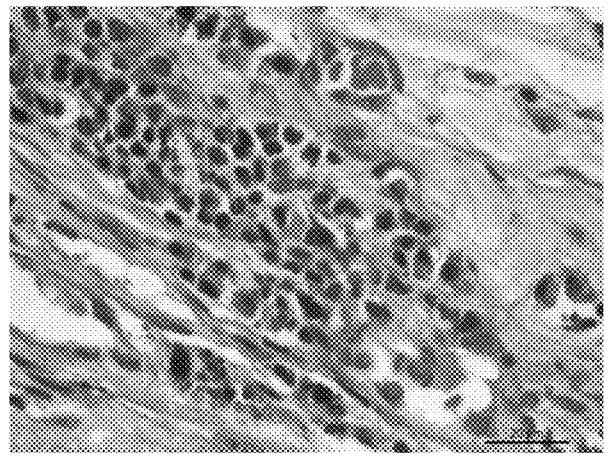
FIG. 7 is a pathological section of a tissue around a vascular stent of Embodiment 5 after the stent has been implanted into a porcine coronary blood vessel for 6 months.

With reference to FIG. 7, a pathological section shows that the vascular tissue around the vascular stent of this embodiment does not generate obvious eosinophilic granulocytes, that is to say, the vascular stent of this embodiment has no obvious sensitization effect on the implantation tissue.

Embodiment 6

A galvanized iron-copper-calcium alloy stent is provided, and the device substrate of the stent contains 97 percent of iron, 1 percent of copper, 0.5 percent of calcium, 0.5 percent of zinc and the balance of inclusion elements. The surface of the stent is subjected to dip-coating in a mixture of polycarbonate and chlortrimeton, thus obtaining a coating with the thickness of 5 μm; the mass ratio of the polycarbonate to the chlortrimeton in the coating is 1:20; and a vascular stent of Embodiment 6 is obtained; and the content of the chlortrimeton drug on the surface of the device substrate is 150 ug/cm$^2$. The vascular stent of this embodiment is implanted into a porcine coronary blood vessel. After 6 months, the stent and vascular tissue where the stent is implanted are taken out, and the vascular tissue is subjected to pathology observation.

Figure 8:
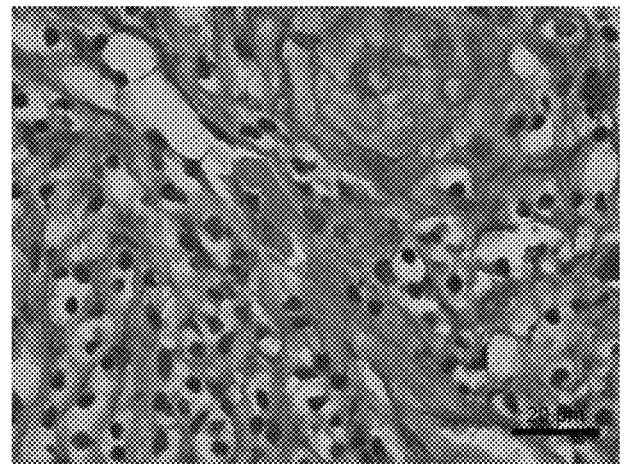
FIG. 8 is a pathological section of a tissue around a vascular stent of Embodiment 6 after the stent has been implanted into a porcine coronary blood vessel for 6 months.

With reference to FIG. 8, a pathological section shows that the vascular tissue around the vascular stent of this embodiment only generates individual eosinophilic granulocytes, that is to say, the vascular stent of this embodiment has no obvious sensitization effect on the implantation tissue.

Embodiment 7

A stent which takes pure zinc as a substrate is provided, the device substrate of the stent contains 100 percent of zinc; part of the surface of the stent is coated with a mixture of polyglycolic acid, mizolastine and taxol using a brushing procedure, thus obtaining a coating with the thickness of 30 μm; the mass ratio of the three components in the coating is 1:10:1, and a vascular stent of Embodiment 7 may be obtained; and the content of the mizolastine drug on the surface of the device substrate is 10 ug/cm$^2$, The vascular stent of this embodiment is implanted into a porcine coronary blood vessel. After 1 month, the stent and vascular tissue where the stent is implanted are taken out, and the vascular tissue is subjected to pathology observation.

Figure 9:
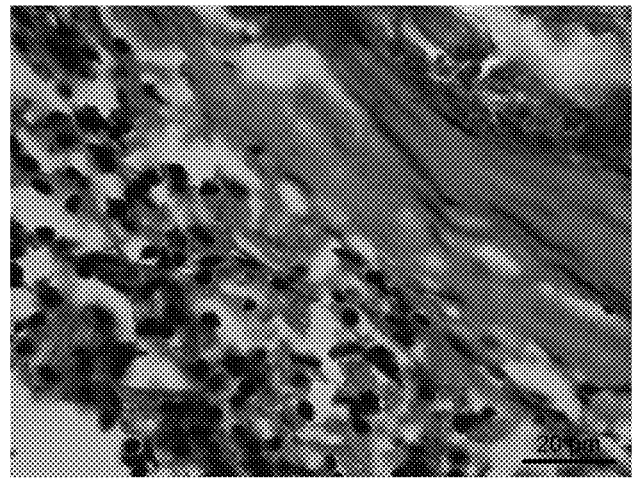
FIG. 9 is a pathological section of a tissue around a vascular stent of Embodiment 7 after the stent has been implanted into a porcine coronary blood vessel for 1 month.

With reference to FIG. 9, a pathological section shows that the vascular tissue around the vascular stent of this embodiment does not generate obvious eosinophilic granulocytes, that is to say, the vascular stent of this embodiment has no obvious sensitization effect on the implantation tissue.

Embodiment 8

An iron-zinc alloy stent is provided, the device substrate of the stent contains 99.9 percent of iron and 0.1 percent of zinc. The surface of the stent is coated with dimercaprol, and then is dried, thus obtaining a vascular stent of Embodiment 8. The vascular stent of this embodiment is implanted into a porcine coronary blood vessel. After 3 months, the stent and vascular tissue where the stent is implanted are taken out, and the vascular tissue is subjected to pathology observation.

Figure 10:
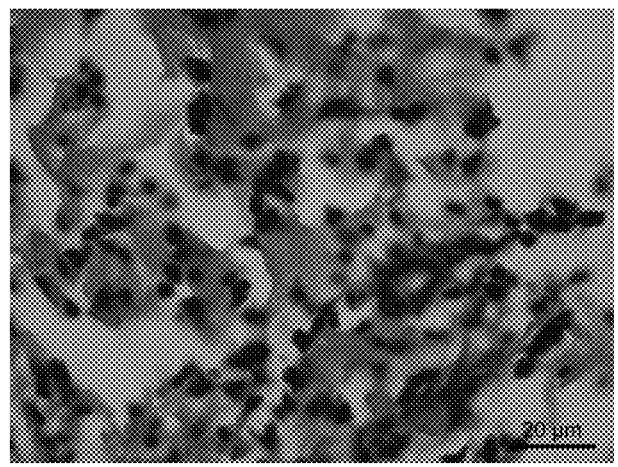
FIG. 10 is a pathological section of a tissue around a vascular stent of Embodiment 8 after the stent has been implanted into a porcine coronary blood vessel for 3 months.

With reference to FIG. 10, a pathological section shows that the vascular tissue around the vascular stent of this embodiment does not generate obvious eosinophilic granulocytes, that is to say, the vascular stent of this embodiment has no obvious sensitization effect on the implantation tissue.

The vascular stent of this embodiment includes the dimercaprol which is capable of generating a complex together with zinc ions: after the vascular stent is implanted into the vascular tissue, the dimercaprol is in complexation with the zinc ions which are corrosion products of the zinc alloy, thereby reducing the concentration of free zinc ions, and no obvious sensitization reaction is caused in the tissue around the implant.

Embodiment 9

A stent which takes pure zinc as a substrate is provided, the device substrate of the stent contains 100 percent of zinc. The outer surface of the stent is rolled in trisodium citrate, thus obtaining a vascular stent of Embodiment 9; the surface of the vascular stent is a non-continuous citric acid coating with the average thickness of 10 μm. The vascular stent of this embodiment is implanted into a porcine coronary blood vessel. After 6 months, the stent and a vascular tissue where the stent is implanted are taken out, and the vascular tissue is subjected to pathology observation.

Figure 11:
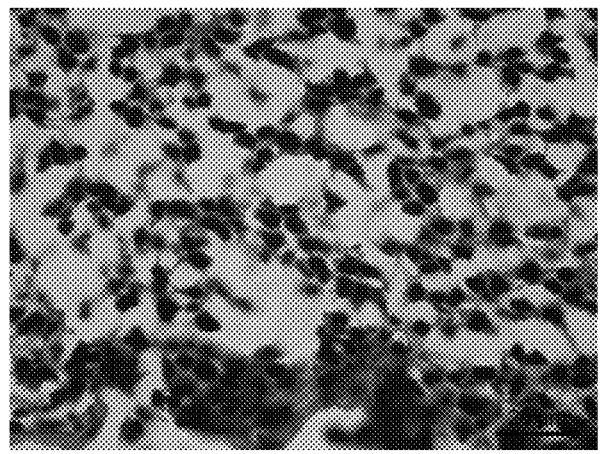
FIG. 11 is a pathological section of a tissue around a vascular stent of Embodiment 9 after the stent has been implanted into a porcine coronary blood vessel for 6 months.

With reference to FIG. 11, a pathological section shows that the vascular tissue around the vascular stent of this embodiment does not generate obvious eosinophilic granulocytes, that is to say, the vascular stent of this embodiment has no obvious sensitization effect on the implantation tissue.

The vascular stent of this embodiment includes the trisodium citrate which is capable of generating a complex together with zinc ions; after the vascular stent is implanted into the vascular tissue, the trisodium citrate is in complexation with the zinc ions which are corrosion products of the zinc alloy, thereby reducing the concentration of free zinc ions, and no obvious sensitization reaction is caused in the tissue around the implant.

In Embodiments 1 to 9, only the zinc-containing vascular stents are used to make a schematic description to specific implementation modes of the present application, and the technical solution provided by the present application also may be applied to other implanted devices, such as a stent, an occluder, an orthopedic implant, a dental implant, a suture line or a bolt. The stent can be a vascular stent, a tracheal stent an esophageal stent, a urethral stent, an intestinal stent or a biliary stent. The orthopedic implant can be a fixing screw, a fixing rivet or a bone plate.

A description is made above to the embodiments of the present application in conjunction with the drawings, but the present application is not limited to the above-mentioned specific implantation modes. The above-mentioned specific implementation modes are merely schematic, but not restrictive. An ordinary person skilled in the art further can make many implementation modes that shall all fall within the protection of the present application under the inspiration of the present application without departing from the purpose of the present application and the scope claimed in claims.

The invention claimed is:

1. An implanted device, consisting of a device substrate that has 95 percent of zinc, 4.5 percent of iron, and 0.5 percent of inclusion elements that do not include zinc or iron; the device substrate has a surface coated with a coating that is a mixture of polylactic acid, dexamethasone, and gluconic acid, with the mass ratio of the polylactic acid to the dexamethasone in the coating being 2:1; wherein the coating on the surface of the device substrate has a thickness of 2 μm, and the content of the dexamethasone on the surface of the device substrate is 100 ug/cm$^2$.

2. The implanted device according to claim 1, wherein the gluconic acid and the zinc in the device substrate form a complex in body fluid.

3. The implanted device according to claim 1, wherein the implanted device is a stent, an occluder, an orthopedic implant, a dental implant, a suture line or a bolt; the stent is a vascular stent, a tracheal stent, an esophageal stent, a urethral stent, an intestinal stent or a biliary stent; and the orthopedic implant is a fixing screw, a fixing rivet or a bone plate.

* * * * *